US006826498B2

(12) United States Patent
Birkner et al.

(10) Patent No.: US 6,826,498 B2
(45) Date of Patent: Nov. 30, 2004

(54) COMPUTERIZED LABORATORY INFORMATION MANAGEMENT SYSTEM

(75) Inventors: Charles Christian Birkner, Magnolia, TX (US); Elias George ElDahdah, Houston, TX (US); Heather Ann Kirkland, Houston, TX (US); David Frederick Martinez, Cypress, TX (US)

(73) Assignee: ATSER, Inc., Houston, TX (US)

( * ) Notice: Subject to any disclaimer, the term of this patent is extended or adjusted under 35 U.S.C. 154(b) by 0 days.

(21) Appl. No.: 09/814,250

(22) Filed: Mar. 21, 2001

(65) Prior Publication Data

US 2002/0138220 A1 Sep. 26, 2002

(51) Int. Cl.[7] .......................... G01N 37/00; G06F 19/00
(52) U.S. Cl. ....................................................... 702/84
(58) Field of Search ............................. 702/81, 84, 127

(56) References Cited

U.S. PATENT DOCUMENTS

| 4,332,158 | A | * | 6/1982 | Osborne .................... 73/54.23 |
| 4,786,331 | A | * | 11/1988 | Ueda et al. .................... 524/8 |
| 5,219,388 | A | * | 6/1993 | Meletiou et al. ......... 73/152.31 |
| 5,614,670 | A | * | 3/1997 | Nazarian et al. ............. 73/146 |
| 5,761,674 | A | | 6/1998 | Ito |
| 5,818,737 | A | | 10/1998 | Orr et al. |
| 5,820,302 | A | * | 10/1998 | Roberts et al. ............. 405/263 |
| 5,861,751 | A | * | 1/1999 | Anderson et al. ........... 324/347 |
| 5,902,068 | A | * | 5/1999 | Angley et al. ................ 404/34 |
| 5,923,726 | A | * | 7/1999 | Regimand .................... 378/207 |
| 5,943,234 | A | * | 8/1999 | Martinez et al. .............. 700/97 |
| 6,301,551 | B1 | * | 10/2001 | Piscalko et al. ............. 702/188 |
| 6,393,410 | B1 | * | 5/2002 | Thompson ................... 705/37 |
| 6,394,242 | B1 | * | 5/2002 | Allaei ........................ 188/378 |
| 2001/0018670 | A1 | * | 8/2001 | Tan et al. ...................... 705/26 |
| 2001/0049634 | A1 | * | 12/2001 | Stewart ....................... 705/26 |
| 2002/0010522 | A1 | * | 1/2002 | Martin .......................... 707/3 |
| 2002/0077717 | A1 | * | 6/2002 | Harburda et al. ............. 700/99 |
| 2002/0077718 | A1 | * | 6/2002 | Harburda et al. ........... 700/106 |
| 2002/0124005 | A1 | * | 9/2002 | Matson et al. .............. 707/101 |
| 2002/0152200 | A1 | * | 10/2002 | Krichilsky et al. ............ 707/3 |
| 2002/0165723 | A1 | * | 11/2002 | Kroger .......................... 705/1 |

OTHER PUBLICATIONS

Russell Lemery Co. Inc., "Home/Products/Software", downloaded from www.ruslem.com/products, 2 pgs, 7/99.

Considering Project Management Software?, Press Release, 2 pgs., downloaded from www.dexterchaney.com/news, 11/99.

* cited by examiner

Primary Examiner—John Barlow
Assistant Examiner—Demetrius Pretlow
(74) Attorney, Agent, or Firm—Tran & Associates (57) ABSTRACT

A computer-implemented system performs quality control on a construction material mixture includes accessing a server located on a wide-area-network; sending information collected from the material mixture to the server; applying one or more test methodologies to the collected information; generating one or more reports from the test methodologies; and sending the one or more reports to a project manager.

20 Claims, 10 Drawing Sheets

COMPUTERIZED LABORATORY INFORMATION MANAGEMENT SYSTEM

COPYRIGHT RIGHTS

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF INVENTION

The present invention relates to a computerized laboratory information management system.

As modern commerce depends on reliable and cost-effective methods for delivering products from suppliers to users, the availability of durable and reliable highways, roads and other support surfaces for vehicles is vital for sustaining a modem economy. To provide better support surfaces, highways, roads, and sidewalks are frequently paved with a layer or mat of asphalt concrete that is laid over the surface of the sub-base.

The concrete needs to be tested. The testing of construction materials is performed as a quality control and quality acceptance function (a quality assurance program) to test materials and workmanship quality. Typically, laboratory testing is performed for materials and in-place inspection is performed for workmanship. Laboratory testing of material quality directly measure the conformance with material specifications.

To ensure that the materials conform to the specification, various tests have been developed for standard test methods for Quality Assurance/Quality Control of soils, aggregates, asphalt, cement asphalt and concrete mixes. The testing technology is rapidly changing due to increasing demands in the material laboratory to provide new levels of service. These new levels of service must be more cost effective to decrease the operating expenditures such as labor cost and the like, and must provide shorter turnaround time of test results as well as improve the accuracy of the analysis. Modernization of analytical apparatus and procedure demands consolidation of workstations to meet the growing challenge placed on the material testing laboratories.

Many construction projects are performed today with contracts that include performance-based specification as part of payment incentives. Tracking quality control and acceptance results on a real-time basis allows contractors to keep material processes within specifications to maximize bonus payments as part the contract payment incentives. Also, real-time quality control tracking allows the contractors for avoid penalties for putting non-conforming material in-place. This reduces the amount of removal of non-conformance materials or minimized the payment penalties for materials outside of specifications.

SUMMARY

In one aspect, a computer-implemented method to perform quality control on a construction material mixture includes accessing a server located on a wide-area-network; sending information collected from the material mixture to the server; applying one or more test methodologies to the collected information; generating one or more reports from the test methodologies; and sending the one or more reports to a project manager.

Implementations of the aspect may include one or more of the following. The method can provide an Internet browser interface to access the server located on the wide-area-network. The computer-implemented method can apply aggregate test methodologies. The aggregate test methodologies can include one or more of the following: Los Angeles Abrasion; Soundness Test; 24 Hours Water Absorption Sand Equivalent; Unit Weight and Voids in Aggregate; Specific Gravity, Water Absorption and Moisture; and Clay Lumps and Friable Particles in Aggregate. The method can include comprising applying soil test methodologies. The soil test methodologies can include one or more of the following: Soil Liquid, Plastic Limit and Plasticity Index; Material in Soil Finer Than #200 Sieve; Moisture and Density of Soil-Aggregate In-Place by Nuclear Method; Moisture Content; Specific Gravity of Soil; Unconfined Compressive Strength of Cohesive Soil; Sieve Analysis; and Compaction Test. The method can include applying asphalt test methodologies. The asphalt test methodologies can include one or more of the following: Extraction; AES300 Emulsion Test; and ARA-1 Rejuvenate Agent. The method can include applying asphalt mix test methodologies, wherein the asphalt mix test methodologies can in turn include one or more of the following: Ignition Test; Actual Specific Gravity; Theoretical Maximum (Rice) Specific Gravity; Tensile Strength Ratio; Marshall Stability; Hveem Stability and Voids Calculation. The method can apply concrete mix test methodologies. The concrete mix test methodologies can include one or more of the following: Unit Weight, Yield, Air Content of Mix; Flexural Strength; Compressive Strength of Cylindrical Concrete Specimens; and Air Content.

Advantages of the system may include one or more of the following. The system allows a user to analyze material testing data from beginning to end using one centralized resource. This makes the material testing process easier to understand for the user and allows the user to control and monitor progress relating to the analysis of the materials.

The system completes a material analysis transaction with many users, keeping track of what each user is doing and progress. The system allows the entire process to be accessible from one central location on a network. The system is also efficient and low in operating cost. It also is highly responsive to user requests.

Other advantages and features will become apparent from the following description, including the drawings and claims.

DESCRIPTION

Referring now to the drawings in greater detail, there is illustrated therein structure diagrams for a laboratory information management system and logic flow diagrams for the processes a computer system will utilize to complete various material tests. It will be understood that the program is run on a computer that is capable of communication with consumers via a network, as will be more readily understood from a study of the diagrams.

Figure 1:
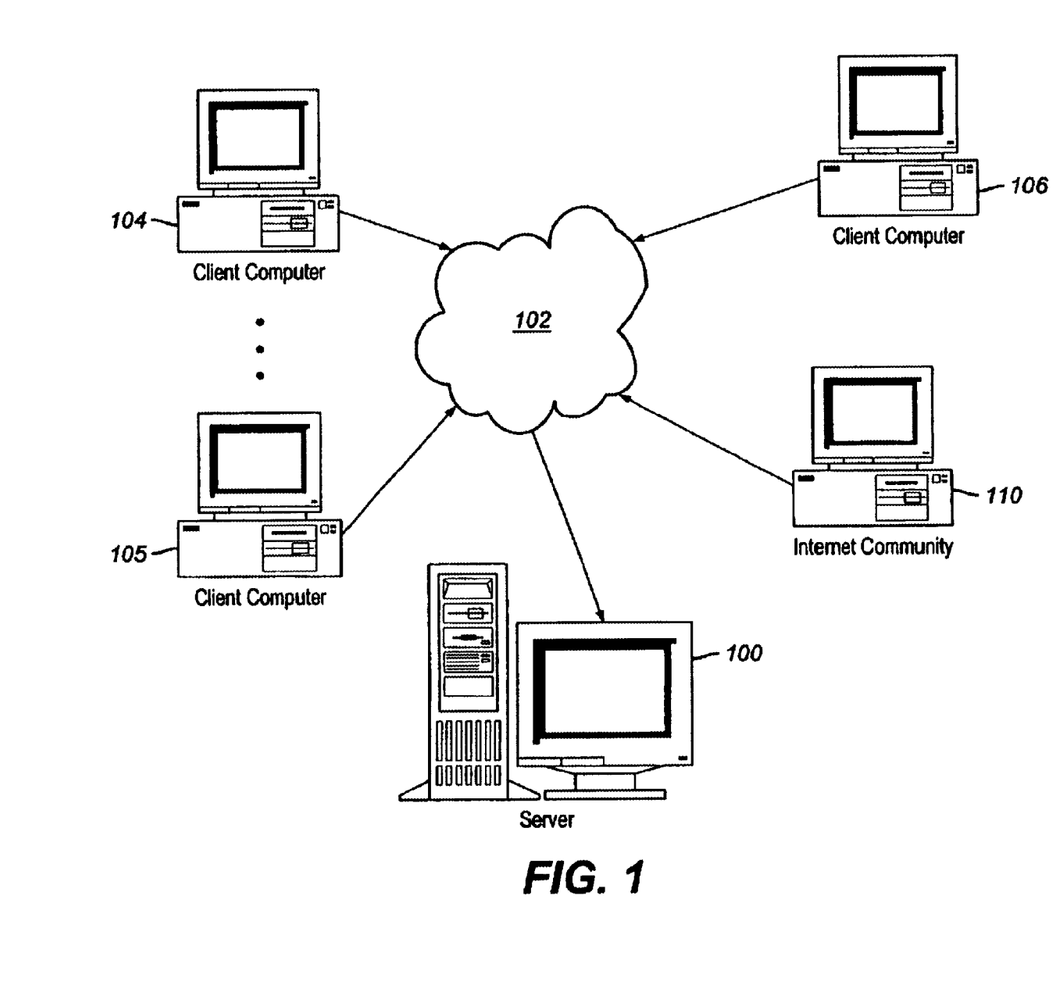
FIG. 1 shows an environment for processing material test quality control or quality assurance transactions.

FIG. 1 shows an environment for processing a laboratory material analysis. A server 100 is connected to a network 102 such as the Internet. One or more client workstations 104–106 are also connected to the network 102. The client workstations 104–106 can be personal computers or workstations running browsers such as Netscape or Internet Explorer. With the browser, a client or user can access the server 100's Web site by clicking in the browser's Address box, and typing the address (for example, www.atser.com), then press Enter. When the page has finished loading, the status bar at the bottom of the window is updated. The browser also provides various buttons that allow the client or user to traverse the Internet or to perform other browsing functions.

An Internet community 110 with one or more building construction companies, service providers, manufacturers, or marketers is connected to the network 102 and can communicate directly with users of the client workstations 104–106 or indirectly through the server 100. The Internet community 110 provides the client workstations 104–106 with access to a network of test service providers.

Although the server 100 can be an individual server, the server 100 can also be a cluster of redundant servers. Such a cluster can provide automatic data failover, protecting against both hardware and software faults. In this environment, a plurality of servers provides resources independent of each other until one of the servers fails. Each server can continuously monitor other servers. When one of the servers is unable to respond, the failover process begins. The surviving server acquires the shared drives and volumes of the failed server and mounts the volumes contained on the shared drives. Applications that use the shared drives can also be started on the surviving server after the failover. As soon as the failed server is booted up and the communication between servers indicates that the server is ready to own its shared drives, the servers automatically start the recovery process. Additionally, a server farm can be used. Network requests and server load conditions can be tracked in real time by the server farm controller, and the request can be distributed across the farm of servers to optimize responsiveness and system capacity. When necessary, the farm can automatically and transparently place additional server capacity in service as traffic load increases.

The server 100 can also be protected by a firewall. When the firewall receives a network packet from the network 102, it determines whether the transmission is authorized. If so, the firewall examines the header within the packet to determine what encryption algorithm was used to encrypt the packet. Using this algorithm and a secret key, the firewall decrypts the data and addresses of the source and destination firewalls and sends the data to the server 100. If both the source and destination are firewalls, the only addresses visible (i.e., unencrypted) on the network are those of the firewall. The addresses of computers on the internal networks, and, hence, the internal network topology, are hidden. This is called "virtual private networking" (VPN).

The server 100 allows a consumer to log onto a computerized laboratory analysis software package incorporating AASHTO and ASTM standard test methods for Quality Assurance/Quality Control of soils, aggregates, asphalt, cement asphalt and concrete mixes. Information relating to the various portions of a transaction are captured and stored in a single convenient location where it can be accessed at any time.

Figure 2:
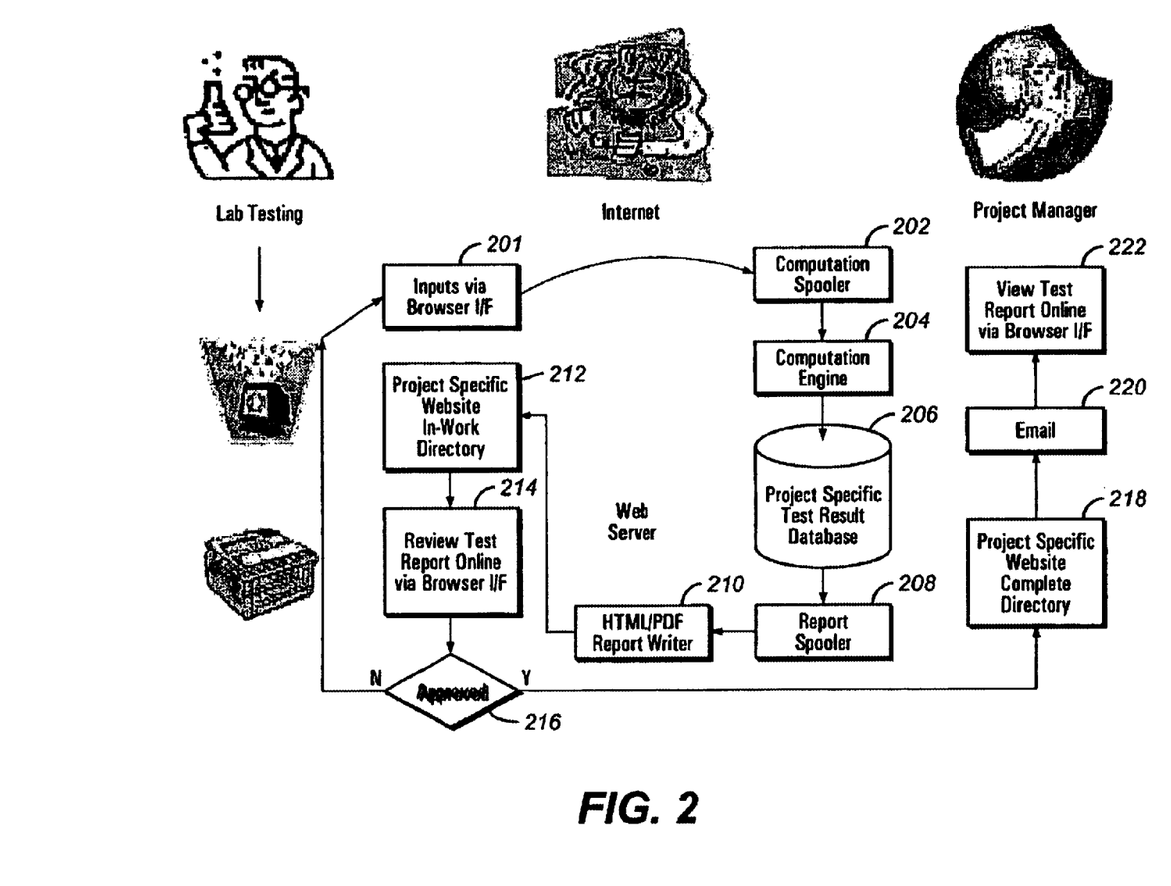
FIG. 2 shows one embodiment of a process for processing material test information.
Figure 3A:
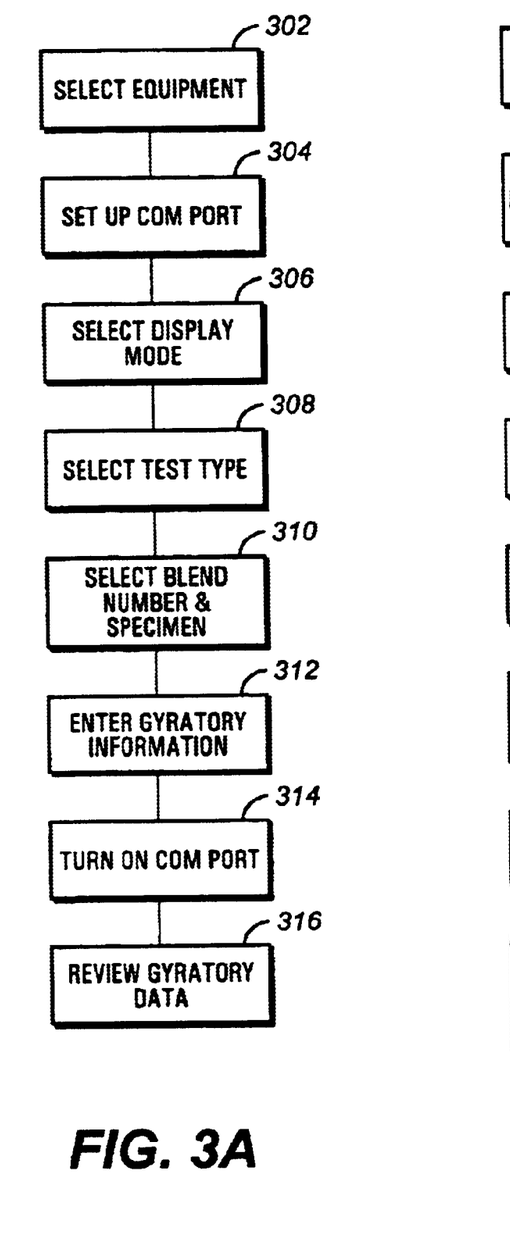
FIGS. 3A–3E show an exemplary process and various exemplary user interfaces for performing gyratory compaction.
Figure 3B:
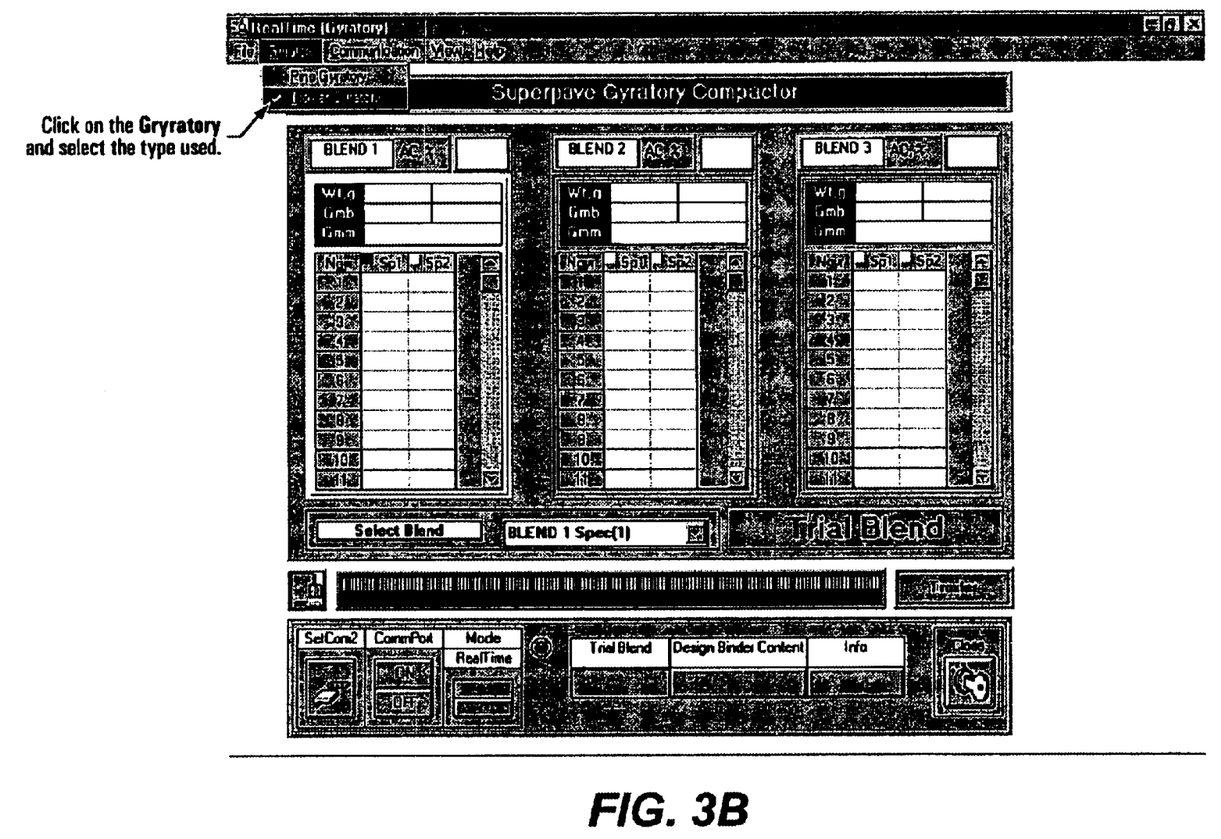
Figure 3C:
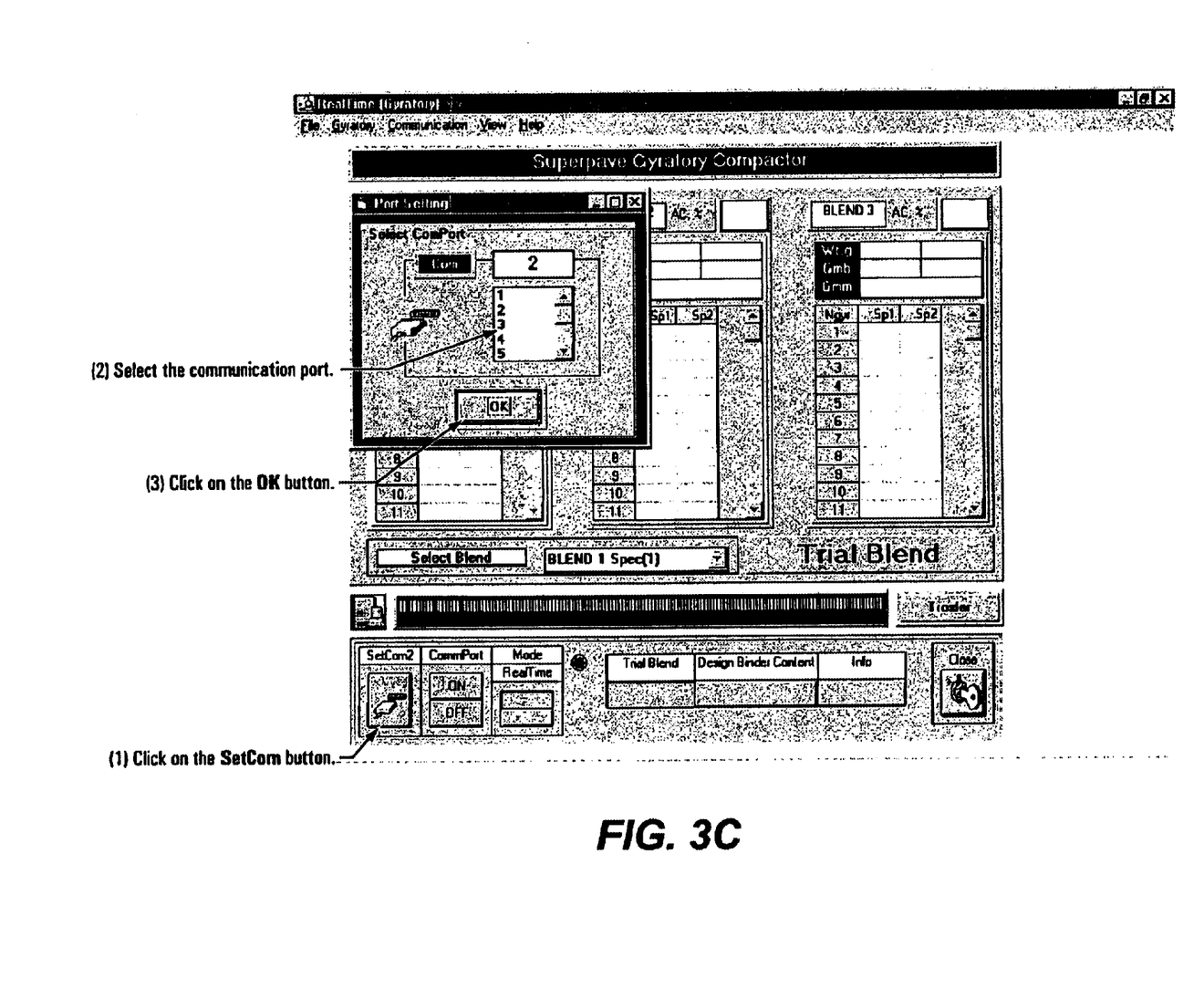
Figure 3D:
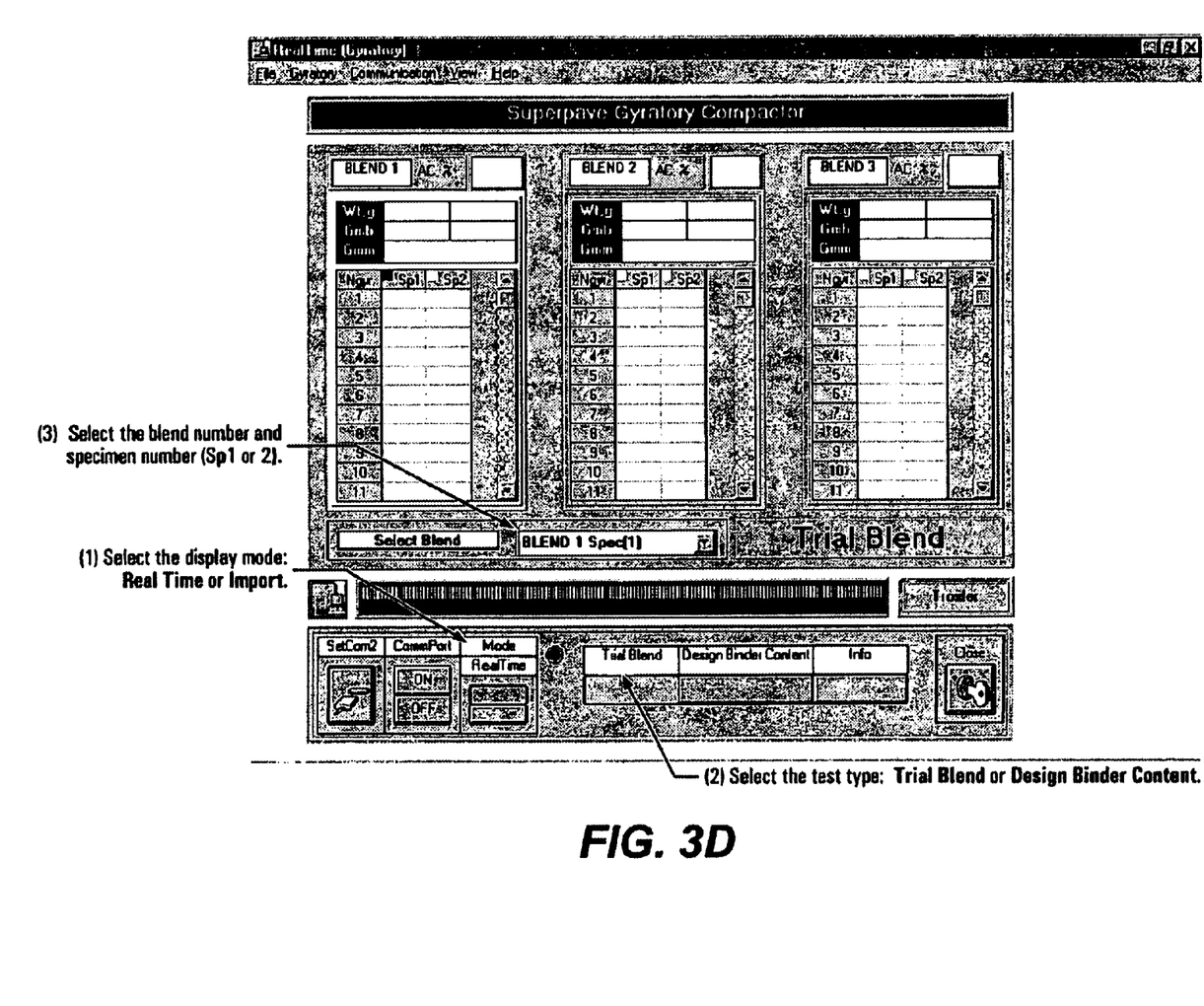
Figure 3E:
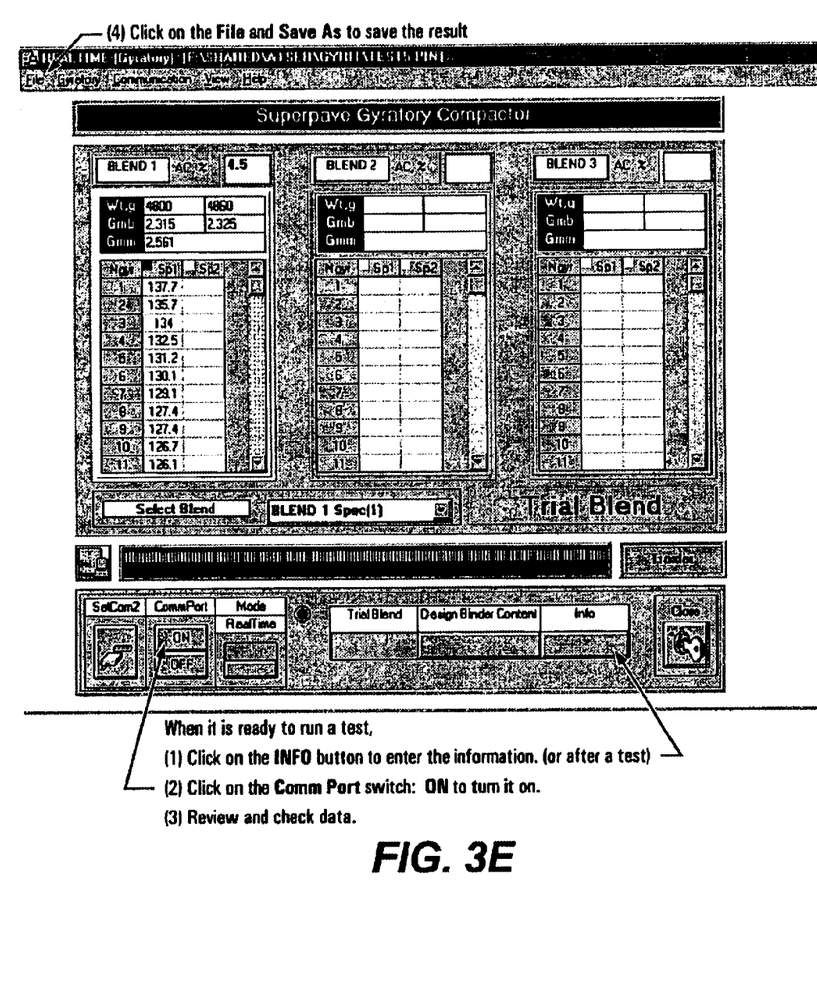

FIG. 2 shows an exemplary process 200 for providing a network-based Laboratory Information Management System (LIMS) on the server 100. First, browser based user interfaces are used to collect test result inputs (step 201). These inputs are collected by the server 100 and provided to a computation spooler (step 202). The spooler activates a computation engine performing the appropriate engineering calculation (step 204) and writes this information to a project specific test result database (step 206). The process 200 then activates a report spooler (step 208). The report spooler then sends output information to a report writer that stores this information in an In-Work directory for each project for review by a lab manager (step 210). In one embodiment, the report writer can generate HTML or PDF documents for viewing.

The lab manager classifies the test results (step 212). Unapproved test results will require updates to the test inputs, recalculation of results, and re-posting of the information to the In-Work website directory. Approved test reports will be promoted to the completed directory on a project specific website. The project specific website directories provide for data security and separation of client's project specific information. The process 200 sends an email notification to a Project Manager for viewing of the final report online (step 214).

The computer-implemented method can apply one or more test methodologies, for example aggregate test methodologies. The aggregate test methodologies can include one or more of the following: Los Angeles Abrasion; Soundness Test; 24 Hours Water Absorption Sand Equivalent; Unit Weight and Voids in Aggregate; Specific Gravity, Water Absorption and Moisture; and Clay Lumps and Friable Particles in Aggregate. The method can include comprising applying soil test methodologies. The soil test methodologies can include one or more of the following: Soil Liquid, Plastic Limit and Plasticity Index; Material in Soil Finer Than #200 Sieve; Moisture and Density of Soil-Aggregate In-Place by Nuclear Method; Moisture Content; Specific Gravity of Soil; Unconfined Compressive Strength of Cohesive Soil; Sieve Analysis; and Compaction Test. The method can include applying asphalt test methodologies. The asphalt test methodologies can include one or more of the following: Extraction; AES300 Emulsion Test; and ARA-1 Rejuvenate Agent. The method can include applying asphalt mix test methodologies, wherein the asphalt mix test methodologies can in turn include one or more of the following: Ignition Test; Actual Specific Gravity; Theoretical Maximum (Rice) Specific Gravity; Tensile Strength Ratio; Marshall Stability; Hveem Stability and Voids Calculation. The method can apply concrete mix test methodologies. The concrete mix test methodologies can include one or more of the following: Unit Weight, Yield, Air Content of Mix; Flexural Strength; Compressive Strength of Cylindrical Concrete Specimens; and Air Content.

By supporting a plurality of test methodologies, the process of FIG. 3 offers a comprehensive laboratory analysis incorporating AASHTO and ASTM standard test methods for Quality Assurance/Quality Control of soils, aggregates, asphalt, cement asphalt and concrete mixes.

The computer-implemented method can apply aggregate test methodologies. The aggregate test methodologies can include one or more of the following: Los Angeles Abrasion; Soundness Test; 24 Hours Water Absorption Sand Equivalent; Unit Weight and Voids in Aggregate; Specific Gravity, Water Absorption and Moisture; and Clay Lumps and Friable Particles in Aggregate. The method can include comprising applying soil test methodologies. The soil test methodologies can include one or more of the following: Soil Liquid, Plastic Limit and Plasticity Index; Material in Soil Finer Than #200 Sieve; Moisture and Density of Soil-Aggregate In-Place by Nuclear Method; Moisture Content; Specific Gravity of Soil; Unconfined Compressive Strength of Cohesive Soil; Sieve Analysis; and Compaction Test. The method can include applying asphalt test methodologies. The asphalt test methodologies can include one or more of the following: Extraction; AES300 Emulsion Test; and ARA-1 Rejuvenate Agent. The method can include applying asphalt mix test methodologies, wherein the asphalt mix test methodologies can in turn include one or more of the following: Ignition Test; Actual Specific Gravity; Theoretical Maximum (Rice) Specific Gravity; Tensile Strength Ratio; Marshall Stability; Hveem Stability and Voids Calculation. The method can apply concrete mix test methodologies. The concrete mix test methodologies can include one or more of the following: Unit Weight, Yield, Air Content of Mix; Flexural Strength; Compressive Strength of Cylindrical Concrete Specimens; and Air Content.

In one implementation, the following aggregate calculations are done. The Los Angeles Abrasion method covers the procedure for testing coarse aggregate for resistance to degradation using the Los Angeles testing machine, as defined in AASHTO T96, ASTM C131. The soundness test measures aggregate resistance to disintegration according to AASHTO T104. The 24 Hour Water Absorption test method covers the determination of specific gravity and absorption of coarse aggregate pursuant to AASHTO T85-91, ASTM C127-88. The sand equivalent serves as a rapid field test to show the relative proportion of fine dust or claylike material in soils or graded aggregates. The Unit Weight and Voids in Aggregate test method covers the determination of unit weight in a compacted or loose condition and calculated and in fine, coarse, or mixed aggregates based on the determination under ASTM C29, AASHTO T19. The specific gravity, water absorption and moisture method is used to determine the bulk specific gravity and water absorption of aggregate retained on a No. 80 sieve, as defined in ASTM T84. The clay lumps and friable particles in aggregate method covers the approximate determination in clay lumps and friable particles in natural aggregates, per AASHTO T112-91. The sieve analysis method is used to determine the particle size distribution of aggregate samples, using sieves with square openings under ASTM C136, ASSHTO T27

For soils, the Soil Liquid, Plastic Limit and Plasticity Index procedure determines the liquid limit of soils, defined as the water content of a soil at the arbitrarily determined boundary between the liquid and plastic states, expressed as a percentage of the oven-dried mass of the soil. It also determines the plastic limit and plasticity index in soil as defined in ASSHTO T89,90,91. The Material in Soil Finer then #200 Sieve method determines the amount of soil material finer than the 75 $\mu$m (No. 200) sieve under AASHTO T11, ASTM D1140. The Moisture and Density of Soil-Aggregate In-Place by nuclear method covers the determination of the total or wet density of soil and soil aggregate in-place by the attenuation of gamma rays. The Moisture Content method covers the laboratory determination of the moisture content of soil under AASHTO T265. The specific gravity of soils method covers the determination of the specific gravity of soils by means of a pycnometer under AASHTO T100-95, ASTM D854-83 The Unconfined Compressive Strength of Cohesive Soil method covers the determination of the unconfined compressive strength of cohesive soil in the undisturbed, remolded, or compacted condition as discussed in AASHTO T208-96, ASTM D2166-85. The sieve analysis of fine and coarse aggregates method covers the determination of the particle size distribution of fine and coarse aggregate by sieving, as discussed in AASHTO T27-97, ASTM C136-95A. The compaction test is intended for determining the relation ship between the moisture content and density when compacted under ASSHTO T99, T180, ASTM D698,D1557. The California Bearing Ratio (CBR) method covers the determination of the (CBR) of pavement subgrade, subbase, and base/course material from laboratory compacted specimens under AASHTO T193-98. The density and unit weight of soil in place by the sand-cone method may be used to determine the in-place density and unit weight of soils using a sand cone apparatus as discussed in ASTM D1556.

For asphalts, the extraction method covers the recovery by the Abson method of asphalt from a solution from a previously conducted extraction (ASTM D1856, ASHTO T170). The emulsion test is described under the headings titled Composition, Consistency, Stability, and examination of residue of ASTM 244, ASSTO T59.

For asphalt mix, the ignition test method covers the determination of asphalt content of hot-mix asphalt (HMA) paving mixtures and paving samples by removing the asphalt content at 540 C by ignition in a furnace, per ASTM D6307-98. The actual specific gravity (Ggm) test method covers the determination of bulk specific gravity of specimens of compacted bituminous mixtures, per AASHTO T166. The theoretical maximum (Rice) specific gravity test method covers the determination of the theoretical maximum specific gravity and density of uncompacted bituminous paving mixtures at 25 C pursuant to AASHTO T209. The tensile strength ratio method covers preparation of the specimens and measurement of the change of diametral tensile strength, per AASHTO T283-89. The Marshall stability test method covers the measurement of the resistance to plastic flow of cylindrical specimens of bituminous paving mixture loaded on the lateral surface by means of Marshall apparatus, per ASTM D1559-89. The Hveem Stability test methods cover the determination of (1) the resistance to deformation of compacted bituminous mixtures by measuring the lateral pressure developed when applying a vertical load by means of Hveem stabilometer, and (2) the cohesion of compacted bituminous mixtures by measuring the force required to break or bend the sample as a cantilever beam by means of the Hveem cohesiometer, per ASTM D1560-92. The voids calculation method covers determination of the percent air voids in compacted dense and open bituminous paving mixtures, as described in AASHTO T269.

The concrete mix test includes the Unit Weight, Yield, and Air Content of Concrete Mix test method that covers determining the weight per cubic meter (cubic yard) of freshly mixed concrete and gives formulas for calculating yield, cement content, and air content of the concrete. Except for editorial differences, this procedure is the same as ASTM C 138 and AASHTO T 121. The Quality of Water to be used in Concrete test method tests for acidity or alkalinity, per AASHTO T26-79. The Compressive Strength of Cylinder Concrete Specimens method covers determining compressive strength of cylindrical concrete specimens such as molded cylinders and drilled cores. The flexural strength of concrete test method covers the determination of flexural strength of concrete by the use of a simple beam with third-point loading, per AASHTO T97-86, and ASTM C78-84. The air content method determines the air content of freshly-mixed concrete by observation of the change in volume of concrete with a change in pressure, as described in AASHTO T152-97 and ASTM C231-91B.

The process of FIG. 2 also includes full automatic report generation capability with forms stored within the system. Graphing capabilities include Proctor, PI test, Control Chart, statistical and standard deviation analysis and others. The software can statistically compare test results. Statistical comparisons are performed by over-plotting the contractors' quality control test results and the owners' quality acceptance results. Statistical test are then performed to evaluate the mean, standard deviation, sample size, test frequencies, cumulative frequencies, percent within-limit, percent out-of-limit, F-test (variability testing), T-test (means testing). These statistical tests are important for contractors and owners to determine pay factor adjustments and to assess the level of owners risk in material acceptance.

As part of the quality control, gyratory compaction tests may be performed. Since the 1930's, gyratory compaction has been used in asphalt mixture design under a procedure developed by the Texas Department of Transportation. The number of gyrations are expected to simulate pavement density at the end of life. The original gyrator compaction procedure was done manually. In the late 1950's-early 1960's, mechanized compactors were developed. These gyrators typically applied gyrations continuously while holding vertical pressure constant. In certain models, gyrations continue until the ratio of height change per revolution decreases below a predetermined limit. Other criteria for applying the gyrations include maintaining a constant angle during compaction, a constant vertical pressure, and a constant rate of gyration.

FIGS. 3A–3E show a process 300 and various user interfaces for performing gyratory compaction. First, the user selects a gyratory equipment type (step 302). The equipment can be a unit commercially available from a variety of vendors, including Test Quip, Inc. of New Brighton, Minn.; Rainhart Company of Austin, Tex.; Pine Instrument Company of Grove City, Pa.; and Troxler Electronic Laboratories, Inc. of Research Triangle Park, N.C. Next, the user sets up communications port with the equipment selected in step 302 (step 304). The user selects a display mode: Real Time or Import from a file (step 306). The user then selects a test type, in this embodiment a Trial Blend type or Design Binder Content type (step 308). Additionally, the user selects a blend number and specimen number (step 310). When the user is ready to run a test, the user clicks on an "Info" button to enter the information on the gyratory session (step 312). This information can also be entered after a test. The user then turns on the communication port (step 314), and review and check data generated by the gyratory equipment (step 316).

Figure 4A:
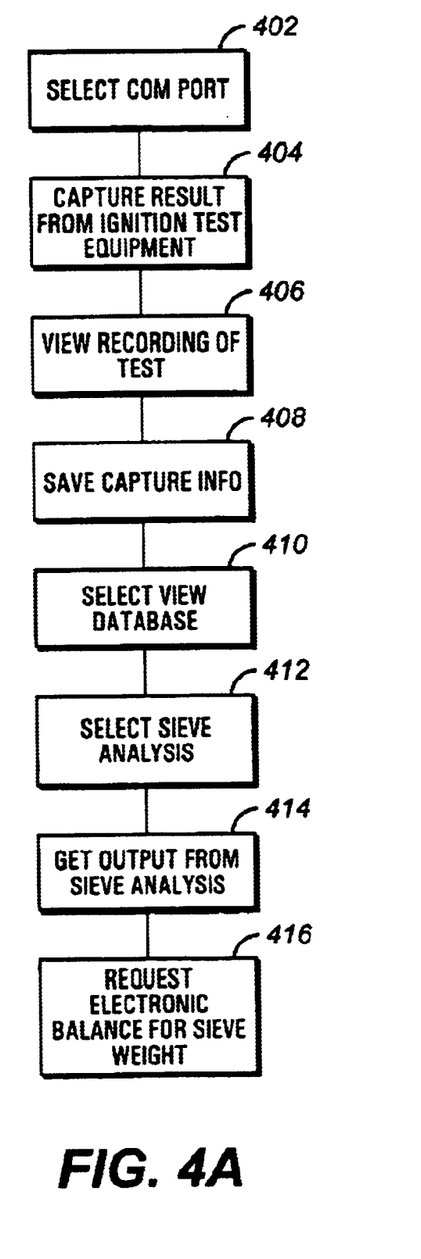
FIGS. 4A–4F show an exemplary process and various exemplary user interfaces for performing ignition tests on materials.
Figure 4B:
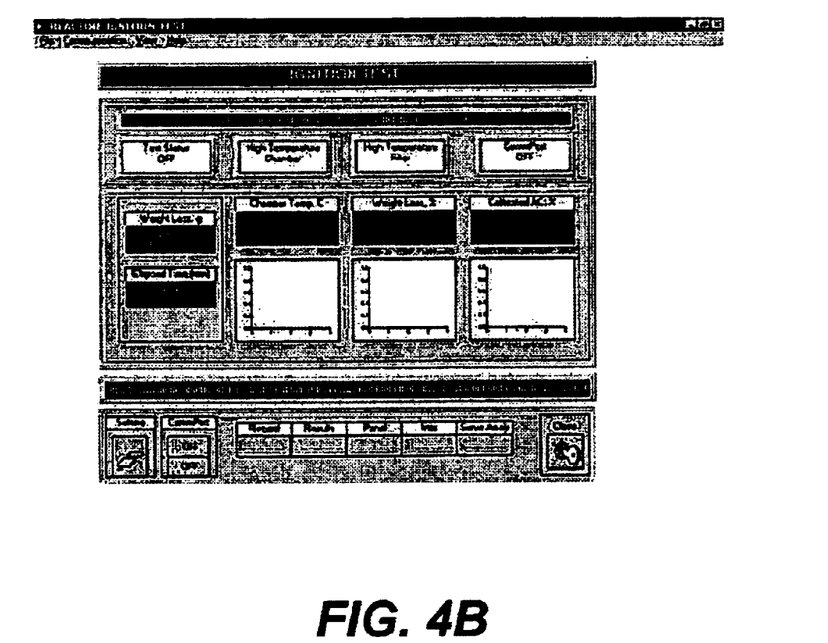
Figure 4C:
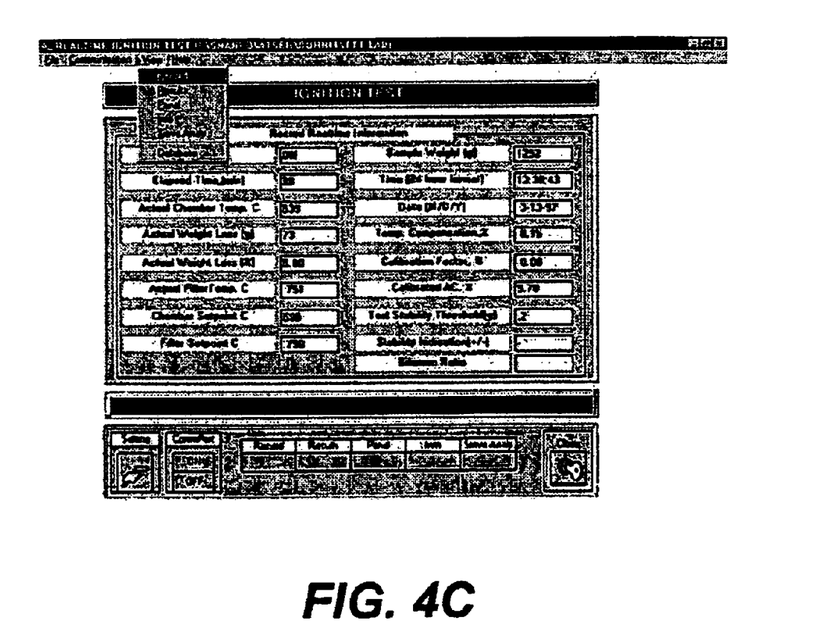
Figure 4D:
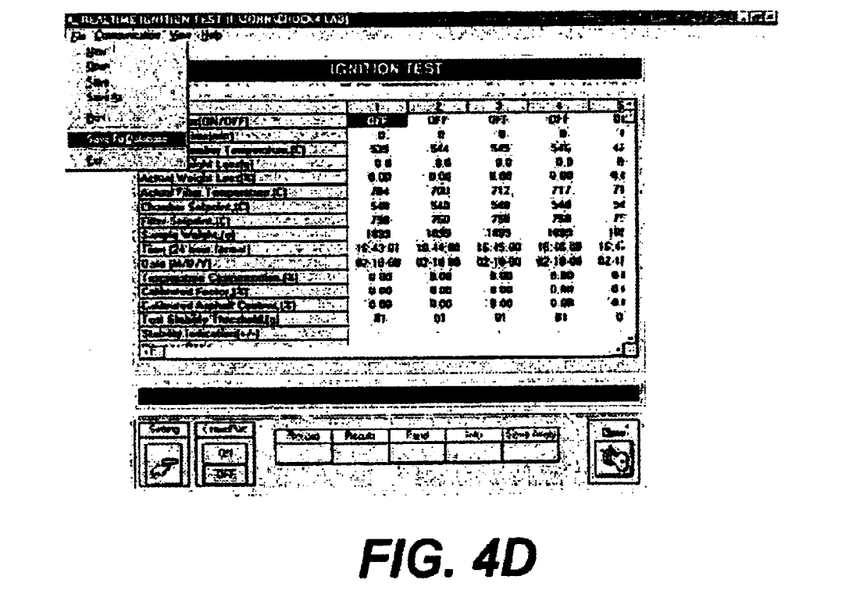
Figure 4E:
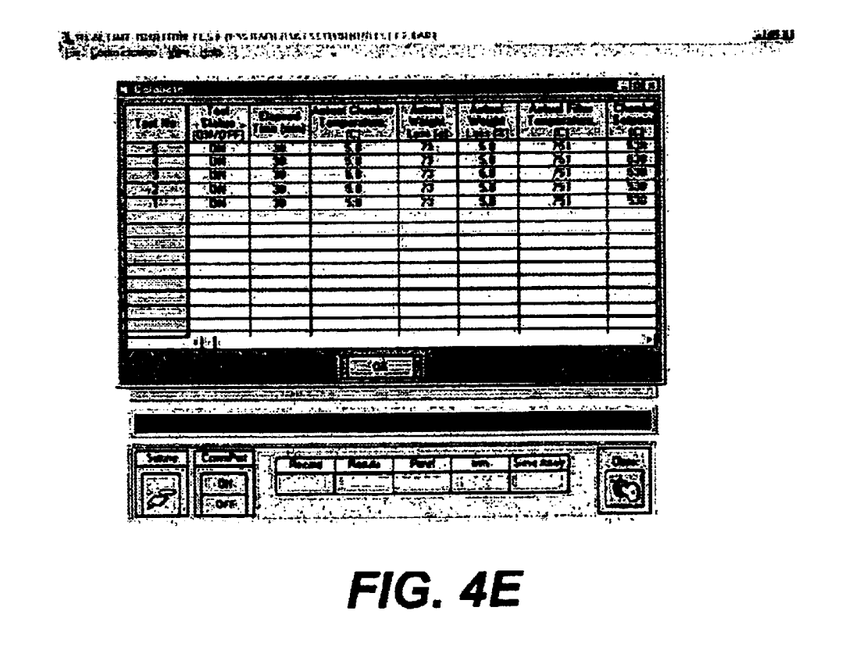
Figure 4F:
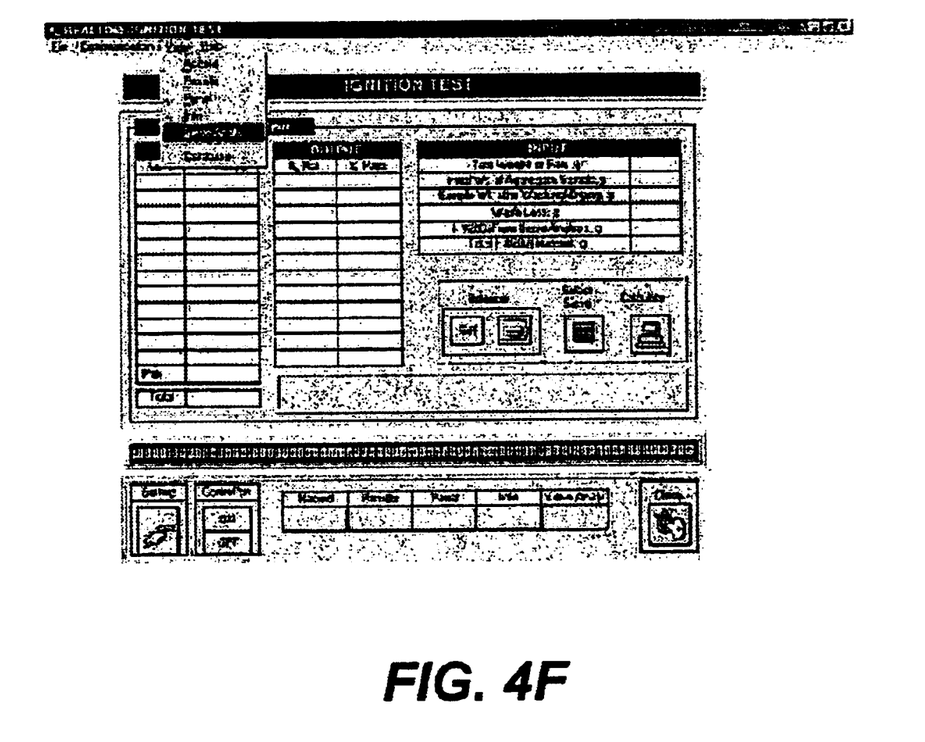

FIGS. 4A–4F show a process 400 and various user interfaces for performing ignition tests on materials. The process 400 supports a communication link between ignition furnaces to record chamber temperature, % weight loss, and calibrated % AC in a real-time tracking mode. In one exemplary implementation, an exemplary user interface is shown in FIG. 4A with a plurality of panel buttons which are also accessible from a menu bar under View. First, the user selects and turns on a particular communication port (step 402). Next, the user can capture the test results from a particular ignition test equipment through the selected port (step 404). In the embodiment of FIG. 4A, clicking on a "RECORD" button allows the user to see the test in real time. The user can also view a by-the-minute recording of the test after it is complete (step 406). In the embodiment of FIG. 4A, this can be done using a "RESULT" button. After completion, the user can save the captured information (step 408). In the embodiment of FIG. 4A, the user can select FILE and the Save from the menu bar to save the test results, first as a sequential file, and then select "Save to Database" to add it to an ignition database. The user can also print results to the printer. Next, the user can select View Database to view the Test results database of all tests completed (step 410). The tests are shown in order from last completed in one embodiment.

The user can also select a "Sieve Analysis" option, which allows the user to input sieve data and track results easily (step 412). After inputting results, the user can select "Calculate" to get output (step 414). The user can also specify a "Balance settings" option to initialize a communications interface to an electronic balance for sieve weights (step 416).

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A computer-implemented method to perform quality control on a pavement construction material mixture, comprising:

accessing a server located on a wide-area-network;

sending information collected from the pavement construction material mixture to the server;

applying one or more test methodologies to the collected information;

generating one or more reports from the test methodologies; and sending the one or more reports to a project manager.

2. The computer-implemented method of claim 1, further comprising applying aggregate test methodologies.

3. The computer-implemented method of claim 2, wherein the aggregate test methodologies include one or more of the following: Los Angeles Abrasion; Soundness Test; 24 Hours Water Absorption Sand Equivalent; Unit Weight and Voids in Aggregate; Specific Gravity, Water Absorption and Moisture; and Clay Lumps and Friable Particles in Aggregate.

4. The computer-implemented method of claim 1 further comprising applying soil test methodologies.

5. The computer-implemented method of claim 4, wherein the soil test methodologies include one or more of the following: Soil Liquid, Plastic Limit and Plasticity Index: Material in Soil Finer Than #200 Sieve; Moisture and Density of Soil-Aggregate In-Place by Nuclear Method; Moisture Content; Specific Gravity of Soil; Unconfined Compressive Strength of Cohesive Soil; Sieve Analysis; and Compaction Test.

6. The computer-implemented method of claim 1, further comprising applying asphalt test methodologies.

7. The computer-implemented method of claim 6, wherein the asphalt test methodologies Include one or more of the following: Extraction; AES300 Emulsion Test; and ARA-1 Rejuvenate Agent.

8. The computer-implemented method of claim 1, further comprising applying asphalt mix test methodologies.

9. The computer-implemented method of claim 8, wherein the asphalt mix test methodologies include one or more of the following: Ignition Test; Actual Specific Gravity; Theoretical Maximum (Rice) Specific Gravity; Tensile Strength Ratio; Marshall Stability; Hveem Stability and Voids Calculation.

10. The computer-implemented method of claim 1, further comprising applying concrete mix rest methodologies.

11. The computer-implemented method of claim 10, wherein the concrete mix test methodologies include one or more of the following: Unit Weight, Yield, Air Content of Mix; Flexural Strength; Compressive Strength of Cylindrical Concrete Specimens; and Air Content.

12. The system of claim 1, further comprising statistically comparing test results in determining pay factor adjustments and material acceptance.

13. A system for performing quality control on a pavement construction material mixture, comprising:
 a wide-area-network;
 one or more client computers coupled to the wide-area-network, each client computer adapted to collect information relating to the pavement construction material mixture properties; and
 a server coupled to the wide-area network, the server applying one or more test methodologies to the collected information; generating one or more reports from the test methodologies; and sending the one or more reports to a project manager.

14. The system of claim 13, further comprising means for applying aggregate test methodologies.

15. The system of claim 14, wherein the aggregate test methodologies include one or more of the following; Los Angeles Abrasion; Soundness Test; 24 Hours Water Absorption Sand Equivalent; Unit Weight and Voids in Aggregate; Specific Gravity, Water Absorption and Moisture; and Clay Lumps and Friable Particles in Aggregate.

16. The system of claim 13 further comprising means for applying soil test methodologies.

17. The system of claim 16, wherein the soil test methodologies include one or more of the following: Soil Liquid, Plastic Limit and Plasticity Index; Material in Soil Finer Than #200 Sieve; Moisture and Density of Soil-Aggregate In-Place by Nuclear Method; Moisture Content; Specific Gravity of Soil; Unconfined Compressive Strength of Cohesive Soil; Sieve Analysis; and Compaction Test.

18. The system of claim 13, further comprising means for applying asphalt test methodologies.

19. The system of claim 18, wherein the asphalt test methodologies include one or more of the following: Extraction; AES300 Emulsion Test; and ARA-1 Rejuvenate Agent.

20. The system of claim 13, further comprising means for applying asphalt mix test methodologies and means for applying concrete mix test methodologies.

* * * * *